United States Patent
Herring

(10) Patent No.: US 8,272,249 B1
(45) Date of Patent: Sep. 25, 2012

(54) AXIAL-GEOMETRY MICRO-DISCHARGE DETECTOR

(75) Inventor: Cyrus M. Herring, Charlotte, NC (US)

(73) Assignee: Cyrus M. Herring, Urbana, IL (US)

( * ) Notice: Subject to any disclaimer, the term of this patent is extended or adjusted under 35 U.S.C. 154(b) by 978 days.

(21) Appl. No.: 12/220,730

(22) Filed: Jul. 28, 2008

Related U.S. Application Data

(60) Provisional application No. 60/962,771, filed on Jul. 31, 2007.

(51) Int. Cl.
*G01N 30/64* (2006.01)
*G01N 30/72* (2006.01)

(52) U.S. Cl. .................. 73/23.4; 73/23.37; 73/31.05

(58) Field of Classification Search .............. 73/23.35, 73/23.37, 23.4, 24.02, 24.06, 31.05, 61.58; 95/82; 96/101; 422/89; 436/161
See application file for complete search history.

(56) References Cited

U.S. PATENT DOCUMENTS

| | | | |
|---|---|---|---|
| 3,656,339 A | 4/1972 | Narain | |
| 3,920,401 A | 11/1975 | Gatiss et al. | |
| 4,794,252 A | 12/1988 | Bateman et al. | |
| 5,036,195 A | 7/1991 | Batey et al. | |
| 5,153,519 A | 10/1992 | Wentworth et al. | |
| 5,281,915 A | 1/1994 | Takahama et al. | |
| 5,317,271 A | 5/1994 | Wentworth et al. | |
| 5,394,091 A | 2/1995 | Wentworth et al. | |
| 5,591,896 A | 1/1997 | Lin | |
| 5,955,886 A | 9/1999 | Cohen et al. | |
| 6,012,326 A | 1/2000 | Raybone et al. | |
| 6,457,347 B1 | 10/2002 | Koo et al. | |
| 6,700,329 B2 | 3/2004 | Giapis et al. | |
| 6,900,734 B2 * | 5/2005 | Duan | 340/632 |
| 7,100,421 B1 | 9/2006 | Herring | |
| 7,401,497 B2 * | 7/2008 | Bonne et al. | 73/23.35 |
| 7,701,578 B1 * | 4/2010 | Herring | 356/417 |
| 2005/0142035 A1 * | 6/2005 | Bonne et al. | 422/82.05 |

* cited by examiner

*Primary Examiner* — Daniel Larkin

(57) ABSTRACT

A detection device capable of giving atomic and molecular compositions of gases made of concentric tubes and a fiber optic. The body of the detector holds these constituents in their relative positions. A micro-discharge is created between two of the concentric tubes at the tip of the device. The small size of the tubes allows a stable discharge to be achieved. The light from this discharge is delivered from the discharge area to an optical sensing device through the fiber optic. The optical sensing device, along with a computer, analyzes the light to determine the composition of the gas in the discharge. Gas and vacuum are applied through the tubes as needed to aid operation. The detector can be battery powered and used in both hot and toxic environments. Alternatively, a voltmeter can be used to measure impedance across the discharge thus providing another means to determine relative changes in gas composition.

43 Claims, 13 Drawing Sheets

AXIAL-GEOMETRY MICRO-DISCHARGE DETECTOR

CROSS-REFERENCE TO RELATED APPLICATION

This application claims the benefit of U.S. Provisional Application Ser. No. 60/962,771, Jul. 31, 2007.

FIELD OF THE INVENTION

This invention pertains to a detector which can identify atomic and molecular components of different gases. More particularly, this invention describes a spectroscopic-based micro-discharge detector used for identification of atomic and molecular compositions of gases and for gas chromatography applications.

BACKGROUND OF THE INVENTION

In industrial gas analysis, extractive gas detection and analysis begins with the collection of gas to be analyzed. This often involves bringing the gas from a hostile environment, such as the inside of a smoke stack, to equipment capable of performing an analysis of the gas, which is usually not in the same environment (i.e., the gas detection equipment is outside the smokestack). The gas is carried through tubing, usually ¼"-stainless steel or plastic. Gas temperature differences between where the gas is sampled (typically >100 degrees Celsius), and where the analysis equipment is located (room or outside temperature) can cause critical components of the sampled gas to condense inside the tubing before reaching the detection equipment. For this reason, the tubing is often heated the entire distance between the sampling point and the detection equipment. Another solution is to introduce a dilution gas into the tubing, along with the sampled gas stream, to prevent condensation of key components of the gas even though the temperature decreases as the gas travels through the tubing. The dilution gas is chosen such that it does not interfere with the detection equipment or the compounds sought to detect, and it often consists of dry air or nitrogen. It is mixed at ratios ranging from twenty to four hundred parts dilution gas to one part sampled gas.

The detection equipment that is employed depends on the application, but often consists of several separate units; each unit detects one compound or one family of compounds. One common detector determines the quantity of nitric oxide (NO) by measuring the intensity of light that is emitted when ozone ($O_3$) is reacted with NO. This common technique is referred to as chemiluminescence and has been the mainstream industry measurement standard for NO concentration since the 1960's. Other pieces of equipment can detect sulfur dioxide ($SO_2$), carbon dioxide ($CO_2$), carbon monoxide (CO), mercury (Hg), and the NO detector can also be configured to detect nitrogen dioxide ($NO_2$).

Other detector technologies using atomic emission techniques have limitations on use, such as Atomic Emission Detectors (AED). These instruments typically sample gas, and then introduce the gas into an inductively coupled plasma (ICP) at low pressure. The instrument is generally limited to bench-top laboratory applications due to its size and power requirements, and it has the complexity of transporting the sampled gas from the source to the low-pressure plasma region. Mass spectrometers (MS) involve a complicated sampling technique to first ionize the sampled gas and then introduce it into a low-pressure analysis chamber. These systems suffer from size and power requirements making economic compact analyzers out of reach.

Still other detection approaches try to measure the gas in the stack environment without transporting it to the equipment. One of these approaches is Laser Induced Breakdown Spectroscopy (LIBS), which needs a relatively expensive laser system for operation. Spectroscopic detector technologies such as fourier transform infrared spectroscopy (FTIR) have size and costs restrictions, and FTIR cannot detect atomic species nor homonuclear species such as Hg, Cd, Se, Cu, Zn, Pb, Ni, $O_2$, $N_2$, $Cl_2$, etc.

Thus a need has long existed for a Axial-Geometry Micro-Discharge Detector that would do all of the following:
1. Be capable of simultaneously detecting a wide variety of molecules and atoms.
2. Be capable of operating on battery power.
3. Be capable of operating in hot and toxic environments.
4. Eliminate the need for sampling lines.
5. Be economical and compact.
6. Not require excessive supporting equipment.
7. Allow adaptation with gas chromatograph equipment.

SUMMARY OF THE INVENTION

This invention is a new detector based on a miniature gas microdischarge. Air or any gas enters the detector (through diffusion or a pressure differential) where it enters a microdischarge. In the microdischarge, the gas emits light that is used to analyze the composition of the gas. The invention is comprised of the following: an optical fiber to deliver light generated by the discharge to an optical detector. This optical fiber is surrounded by an electrically conductive tube (the "inner" tube) that serves both to support the fiber and as an electrode for the gas discharge. This inner tube is surrounded by an electrically insulating tube, which in turn is surrounded by another electrically conductive tube (the "outer" tube) that serves as the other electrode for the gas discharge. Between each of the tubes and between the inner tube and fiber is a small space through which gas flows. One end of these tubes (and fiber) has a means for fixing their relative position, in addition to a means of applying a different voltage to the two conductive tubes, in addition to a means of directing the gas flow in the space between the tubes or between the inner tube and fiber. It is this end of the detector where the fiber connects to the optical sensing equipment. The other end of these metal tubes is where the gas discharge is formed, in the gas surrounding the ends of the metal tubes. The gas discharge emits light that has specific characteristics of the gas in the discharge, just as the characteristic red-orange glow of a neon sign indicates the presence of neon in the glass tube. The light is carried to an optical detector by means of the optical fiber. Typically, a computer will analyze the data from the optical detector to identify the type and concentration of gases in the discharge. An alternate embodiment would monitor relative changes in time of the gas composition by determining gas impedance as measured by the electric voltage and current to the discharge. In this instance, the optical fiber and optical detector are not needed.

These and other features of the present invention are discussed or apparent in the following detailed description.

DETAILED DESCRIPTION OF INVENTION

Figure 1:
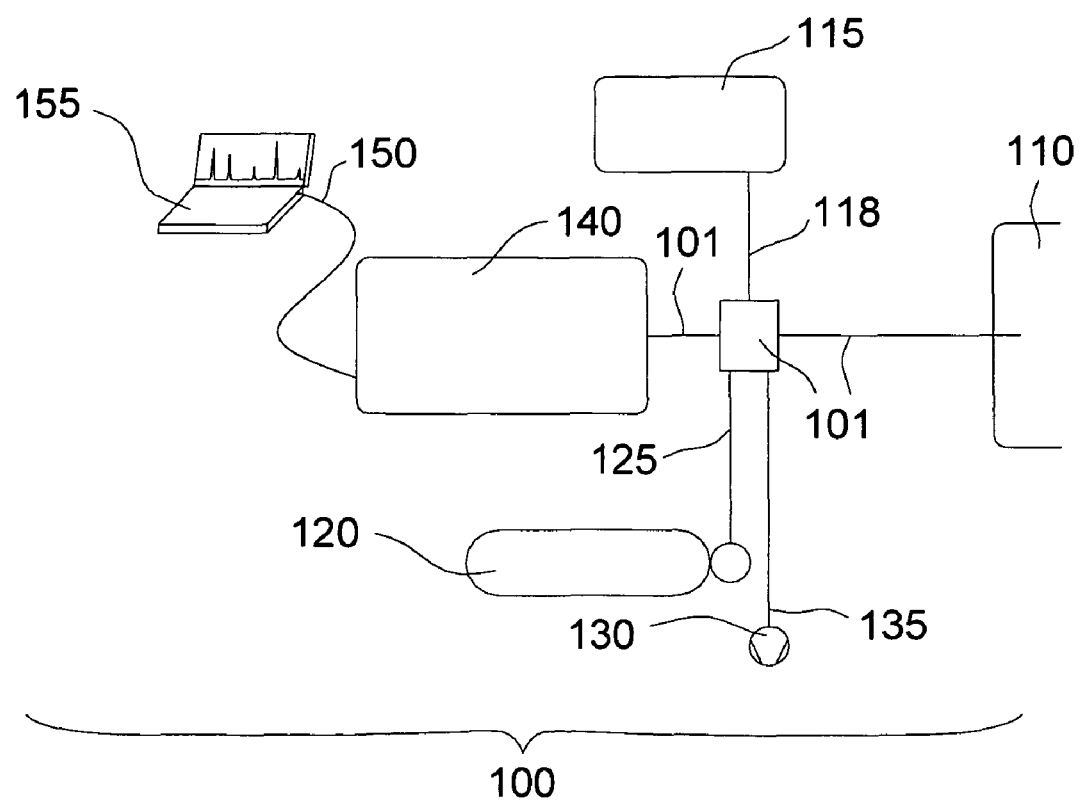
FIG. 1 illustrates a view of a detection system according to an embodiment of the present invention.

FIG. 1 illustrates a schematic of a detector system 100. The detector system 100 consists of a detector 101, power supply 115, power cord 118, gas supply 120, gas supply tube 125, vacuum pump 130, vacuum tube 135, optical sensing device 140, communication cord 150, and computer 155. The detection target 110 is any gaseous source in need of monitoring specific properties of the gas.

The power supply 115 is a small battery powered device, with 2 C-cells providing enough power for twenty-four hours of continuous operation. Alternatively, the power supply 115 is sized and receives the power required to operate the needs of detector system 100. A stabilizing ballast resistor (ranging from 100 k to 10M Ohms) is also included in the electrical circuit. The computer 155 is a laptop. Alternatively, the computer 155 is a more compact integrated electronics included in the detection system enabling analysis in a stand alone portable instrument. As an additional alternative, the computer 155 is any electronic device, of any size, that meets the needs of the detector system 100. A unique feature of the detector system 100 is that the power requirements are small enough to use battery power. Accordingly, the detector system 100 can be mobile and easily installed.

In the detector system 100, a portion of the detector 101 is inside the detection target 110. The detector 101 is electronically connected to the power cord 118 and optically connected to the optical sensing device 140. The power cord 118 is electrically connected to the power supply 115. The detector 101 is also connected to the gas supply tube 125 and vacuum tube 135. The gas supply tube 125 is connected to the gas supply 120. The vacuum tube 135 is connected to the vacuum pump 130. The optical sensing device 140 is electronically connected to the communication cord 150, which is electronically connected to the computer 155.

In operation of the detector system 100, the detector 101 receives electric power from the power cord 118, which receives power from the power supply 115. The detector 101 receives gas from the gas supply tube 125, which receives gas from the gas supply 120. The detector 101 receives vacuum from the vacuum tube 135, which receives vacuum from the vacuum pump 130.

The portion of the detector 101 inside the detection target 110 generates an optical signal, which is received by the optical sensing device 140. The computer 155 communicates with the optical sensing device 140. The computer 155 serves as an interface for the user, allowing the user to operate and obtain results or data from the optical sensing device 140 and detector system 100. The content of the atmosphere in the detection target 110 is determined using the theory of operation described below.

Figure 2:
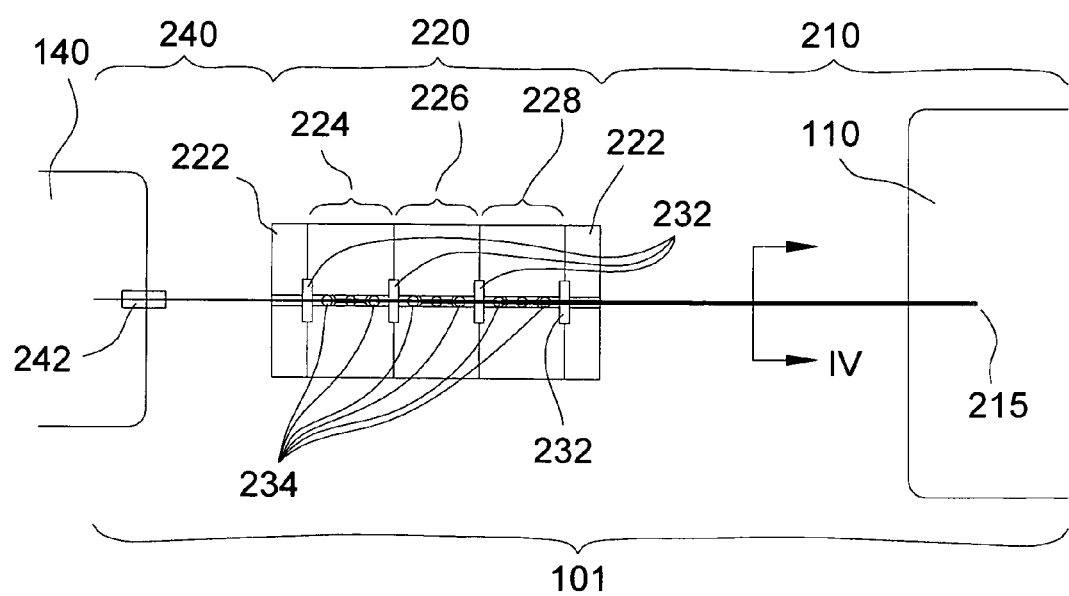
FIG. 2 illustrates a top view of the detector according to an embodiment of the present invention.

FIG. 2 illustrates a top view of the detector 101. The detector 101 consists of a probe 210, body 220, and optical output 240. The probe 210 and optical output 240 are connected to and extend from opposite ends of the body 220.

Figure 3:
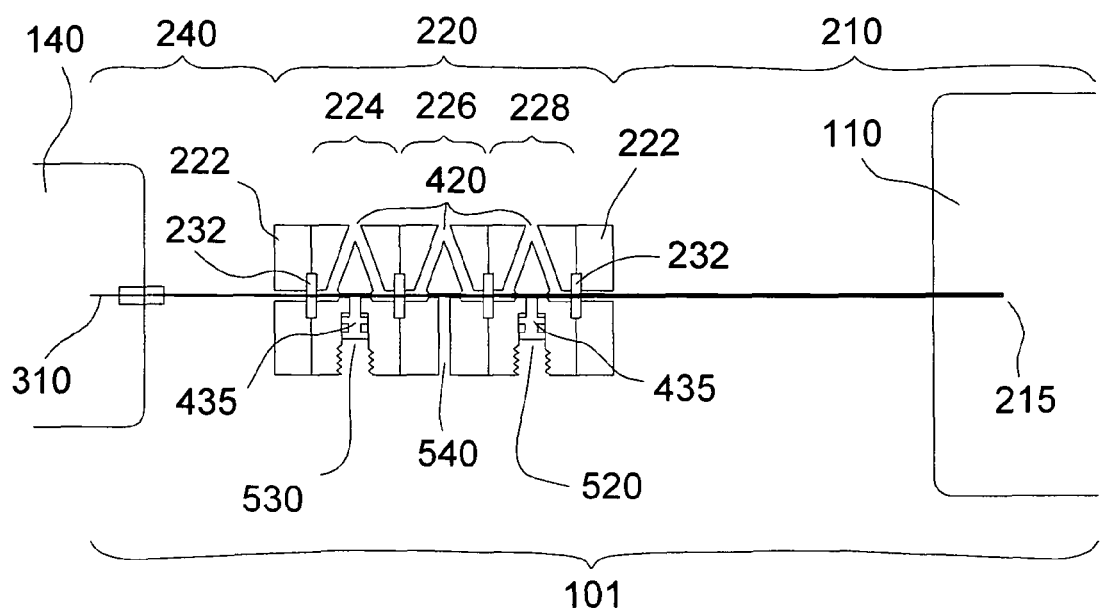
FIG. 3 illustrates a side view of the detector according to an embodiment of the present invention.

FIG. 3 illustrates a side view of the detector 101. The body 220 consists of end plates 222, outer tube holder 224, insulator tube holder 226, inner tube holder 228, rubber gaskets 232, orifices 234, transfer tubes 420, inner tube electric contact 520, view port 540, outer tube electric contact 530, and metal plungers 435.

The outer tube holder 224, insulator tube holder 226, and inner tube holder 228 are located between and connected to the end plates 222. The rubber gaskets 232 are located between and in contact with the outer tube holder 224, insulator tube holder 226, inner tube holder 228, and end plates 222. The transfer tubes 420 are contained within the outer tube holder 224, insulator tube holder 226, and inner tube holder 228. The inner tube electric contact 520 is within the inner tube holder 228 and comprised of a metal plunger 435, which is in contact with the inner tube (320 in FIG. 4). The view port 540 is contained within the insulator tube holder 226. The outer tube electric contact 530 is contained within the outer tube holder 224 and is comprised of a metal plunger 435, which is in contact with the outer tube (340 in FIG. 4).

Figure 4:
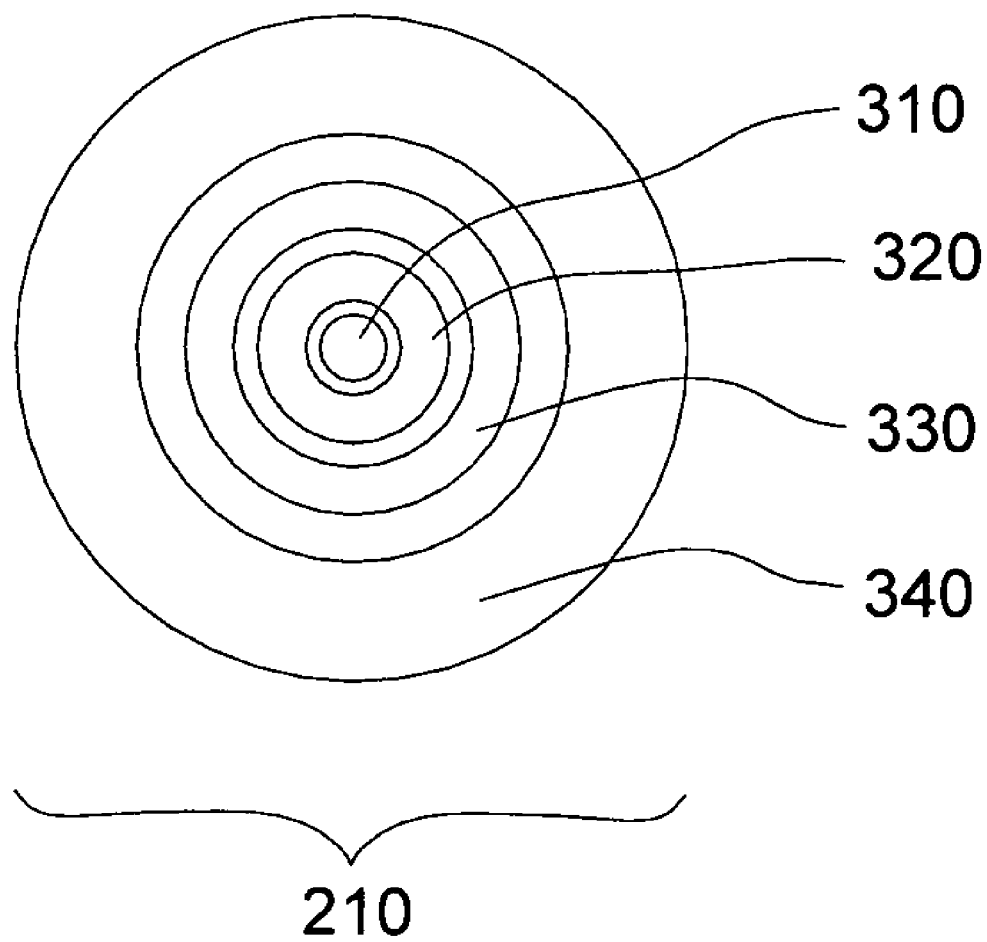
FIG. 4 illustrates an axial-cross sectional view of the probe according to an embodiment of the present invention.

FIG. 4 illustrates a cross sectional view of the probe 210. The probe 210 consists of concentric tubes; an inner tube 320, insulator tube 330, and outer tube 340. The probe 210 also consists of a fiber optic 310 and tip (215 in FIG. 5). The tip 215 is the portion of the probe 210 at the end furthest from the body 220. The tip 215 extends into the detection target 110. At the center of the probe 210 is the fiber optic 310. Surrounding the fiber optic 310 is the inner tube 320. Surrounding the inner tube 320 is the insulator tube 330. Surrounding the insulator tube 330 is the outer tube 340.

Figure 5:
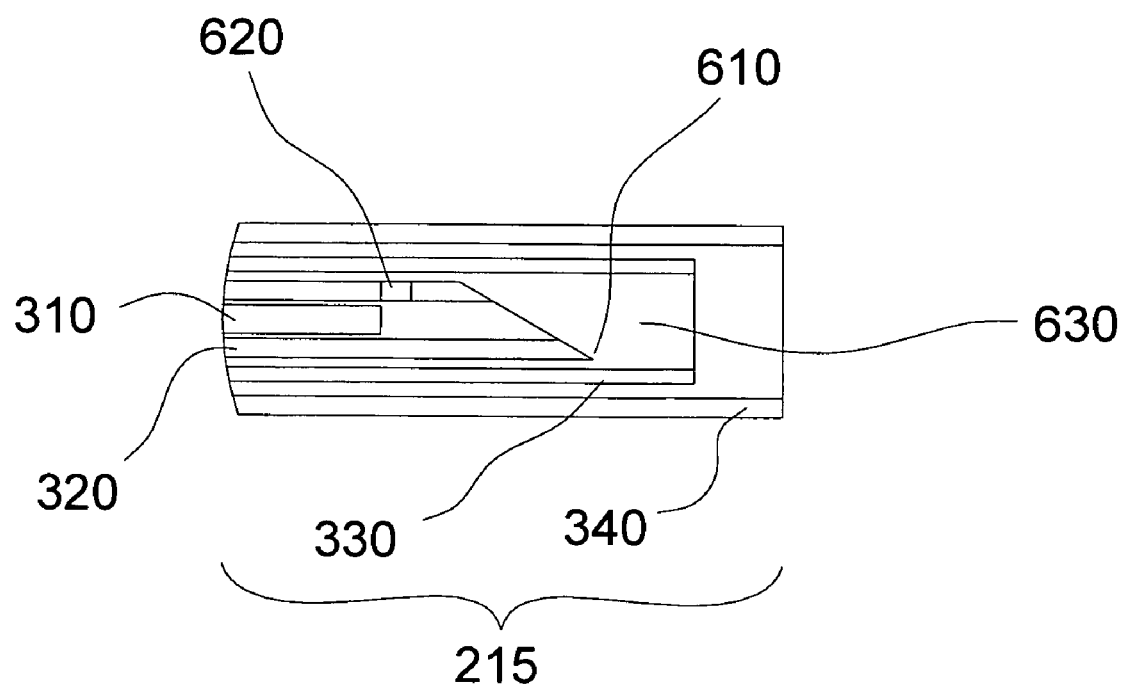
FIG. 5 illustrates a parallel-cross sectional view of the probe tip according to an embodiment of the present invention.

FIG. 5 illustrates a cross sectional view of the tip 215. The tip 215 is the end portion of the probe 210 and is inside the detection target 110. Terminating first is the fiber optic 310. The inner tube 320 extends past the fiber optic 310. The end of the inner tube 320 may be angled to create a discharge point 610 to aid in discharge initiation. The insulator tube 330 extends past the inner tube 320 and discharge point 610. The outer tube 340 extends past the insulator tube 330 and is open to the atmosphere of the detection target 110. The discharge area 630 is the open space between the end of the fiber optic 310 and the point of contact of the end of the insulator tube 330 and outer tube 340. Discharge hole(s) 620 may be added to the end of the inner tube 320 or outer tube 340 to aid in discharge stability.

Figure 6:
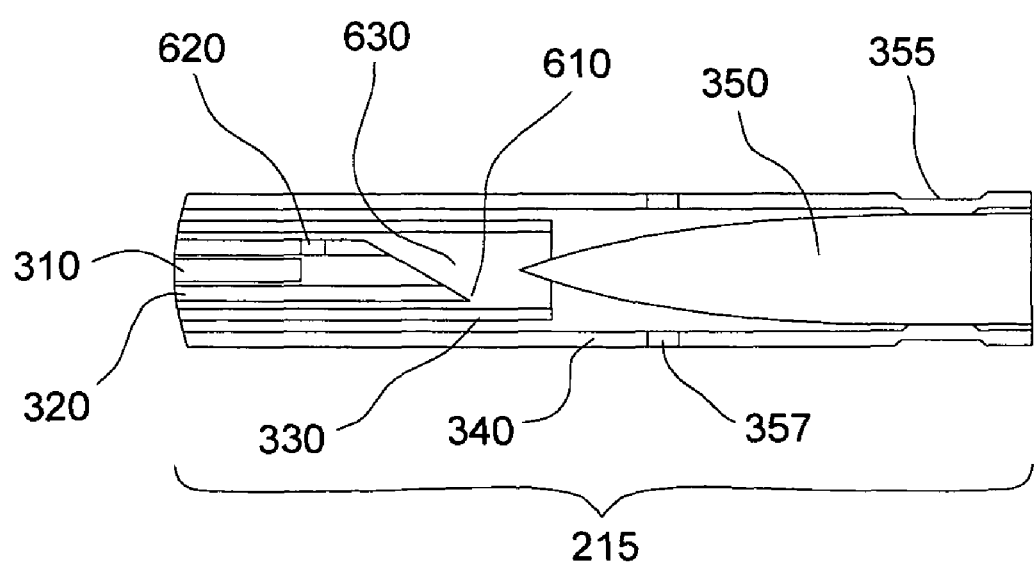
FIG. 6 illustrates a parallel-cross sectional view of an alternative probe tip with an added electrode tip according to an embodiment of the present invention.

FIG. 6 shows an alternative electrode tip 215. In this illustration a sharpened needle (electrode tip) 350 is inserted inside outer tube 340 up to or inside the insulator tube 330. This needle is fixed in place by crushing or deforming the support tube 355 thereby compressing it around the electrode tip 350 to keep it in place and provide electrical contact between the needle tip and outer tube 340. This sharpened metal tip is used to improve electric discharge characteristics as well as reducing operating and starting voltage. Gas flow ports 357 may be drilled into the outer tube 340 to help gas to enter the discharge area 630.

Figure 7:
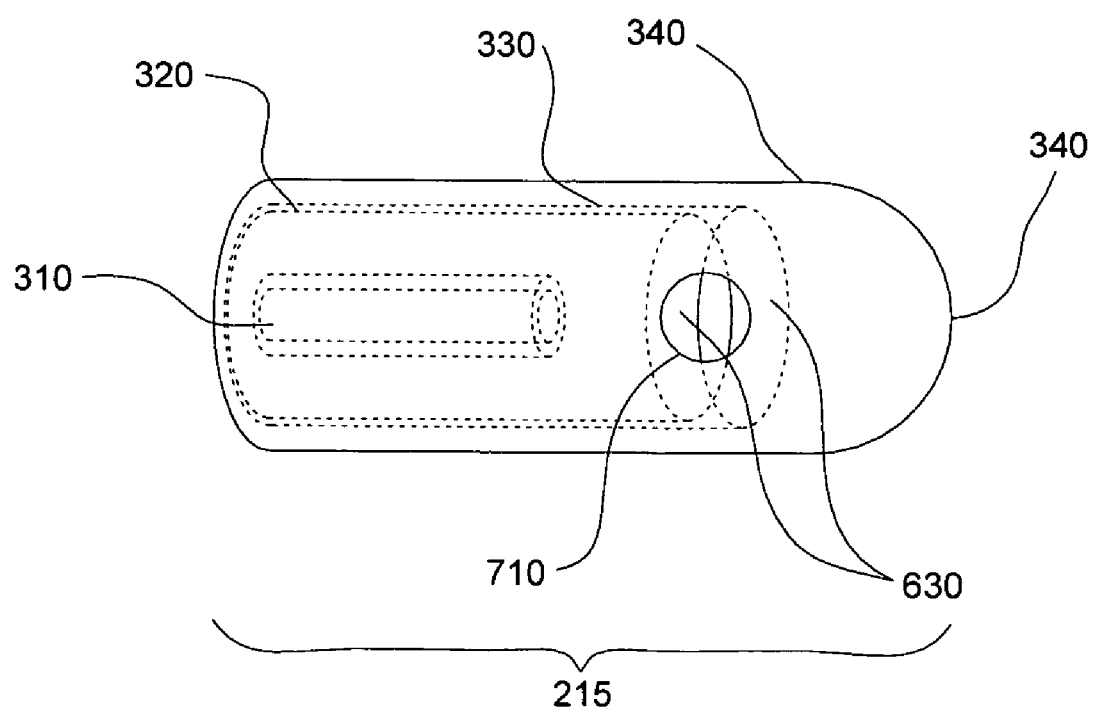
FIG. 7 illustrates a parallel-cross sectional view of an alternative probe tip according to an embodiment of the present invention.

FIG. 7 illustrates a cross sectional view of an alternative tip 215. The end of the inner tube 320 is not angled, creating no discharge point 610. The port 710 is an orifice in the outer tube 340, which allows gas to be introduced into the tip 215 and discharge area 630 from the detection target 110 atmosphere. Alternatively, a filter is introduced, through which the air from the detection target 110 atmosphere must pass before entering the tip 215 and discharge area 630. The end of the outer tube 340 forms the end of the tip 215, creating a cap 720.

The fiber optic 310 typically has an outside diameter of 50 to 100 microns. However, a larger diameter fiber collects more light making a more sensitive instrument. The protective polyimide coating normally found on a fiber optic 310 is removed from fiber optic 310 in the probe 210 to allow high temperature operation. The fiber optic 310 is a 0.22 numerical aperture fiber, or other fiber capable of collecting light from the discharge for analysis. The inner tube 320 is made from type-316 stainless steel, or other electrically conductive material. The inner tube 320 has an inner diameter of 100 microns and an outer diameter of 200 microns. The insulator tube 330 is made from fused silica or quartz, or other dielectric, insulating material. The insulator tube 330 has an inner diameter of 250 microns and an outer diameter of 350 microns. The outer tube 340 is made from type-316 stainless steel, or other electrically conductive material. The outer tube 340 has an inner diameter of 400 microns and an outer diameter of 710 microns. The materials used for the probe 210 allow it to withstand high temperatures, which may be in excess of 1100° C. Thicker outer tubing provides more rigidity and is preferred. Alternatively, an additional tube or tubes are added around the outside for added support and rigidity. Smaller diameter tubes are suited to higher pressure operation, and larger diameters are suited for lower pressure operation. The diameters listed have produced stable results in approximately 1 Torr to 1000 Torr environments, including sampling at atmospheric pressure. The length of the probe 210 is adjusted according to the application and can be meters long.

Alternatively, the insulator tube 330 is removed. The insulator tube 330 is replaced by a coating applied to either the outside of the inner tube 320, or inside of the outer tube 340. The coating is spray-on boron nitride, or other dielectric or electrically insulating coating to prevent electrical contact between the inner tube 320 and outer tube 340.

Figure 8:
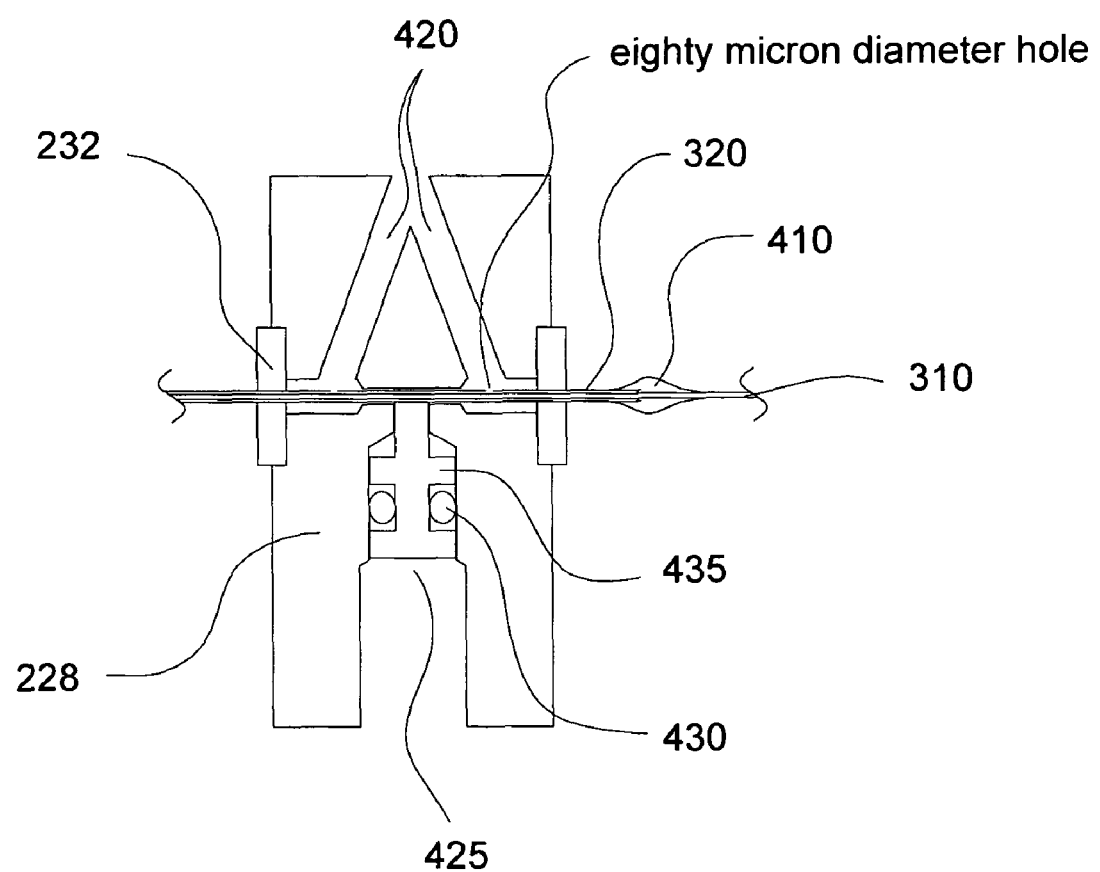
FIG. 8 illustrates a cross sectional view of an individual tube holder to an embodiment of the present invention.

FIG. 8 illustrates a cross sectional view of the inner tube holder 228 showing seals used to make an airtight passage for gas to travel from the transfer tubes 420 into the space between the fiber and inner tube. The inner tube holder 228 is made of metal or an electrically insulating material. A screw 425 placed in the hole below the metal plunger 435 provides pressure against the inner tube 320 so it cannot move as well as provide electrical contact. The sealant 410 prevents any gas from escaping the inner tube 320 towards the optical sensing device 140. Small holes are drilled in the inner tube 320 to allow gas to flow from transfer tubes 420 into the space between the fiber optic 310 and inside of the inner tube 320, in this case 80 microns in diameter.

In operation of the detector 101, the body 220 fixes the relative positions of the inner tube 320, insulator tube 330, and outer tube 340. The inner tube holder 228 is shaped and sized to hold the inner tube 320 in position around the fiber optic 310. The insulator tube holder 226 is shaped and sized to receive and hold the insulator tube 330 in position around the inner tube 320. It is held fixed by compression of the rubber gasket 232 between outer tube holder 224 and insulater tube holder 226. The outer tube holder 224 is shaped and sized to receive and hold the outer tube 340 in position around the insulator tube 330. The rubber gaskets 232 also help to hold the tubes in place. The inner tube holder 228, insulator tube holder 226, and outer tube holder 224 are made of an insulating material or designed in such a way to electrically isolate the inner tube 320 and outer tube 340 from each other. The end plates 222 have screws running between each other, which are used to compress and hold the components of the body 220 together.

Alternatively, no insulator tube holder 226 is included in the body 220. In this case the rubber gaskets 232 between the inner and outer tube holders holds the insulating tube in place. The inside of the insulator tube 330 is in fluid contact with the gas inside the inner tube holder 228 and gas flow will be controlled between the pressure difference between the inner tube holder 228 and discharge area 630. Also, when the insulator tube 330 is replaced by an insulating coating, no insulator tube holder 226 is needed. Additionally, the transfer tubes 420 within insulator tube holder 226 and view port 540 that enter the insulator tube holder 226 are absent in this case.

In operation of the detector 101, the body 220 applies an electric potential between the inner tube 320, and outer tube 340. The power supply 115 delivers an electric potential through the power cord 118 and to the inner tube electric contact 520 and outer tube electric contact 530. The inner tube electric contact 520 makes contact with the inner tube 320 and the outer tube electric contact 530 makes contact with the outer tube 340, delivering an electric potential between both tubes. The electric potential is a direct current (DC) with a 0.50 mA current, with 150 to 350 volts across the discharge or plasma. The amount of current is adjusted to cause a stable plasma to form. Alternatively, the electric potential is alternating current (AC), or cyclic pulsed current. The current used is a current great enough to cause a plasma to form at the discharge area 630 at the tip 215. The stabilizing ballast resistor is sized to prevent excessive current, which would cause the plasma to form an arc that sputters and heats the metal tubes.

The inner tube electric contact 520 is threaded into the inner tube holder 228 where it presses against an O-ring-sealed 430 metal plunger 435 within the inner tube holder 228. The inner tube electric contact 520 includes a metal plunger 435 to make electric contact with the inner tube 320. The outer tube electric contact 530 is threaded into the outer tube holder 224 where it presses against an O-ring-sealed 430 metal plunger 435 within the outer tube holder 224. The outer tube electric contact 530 includes a metal plunger 435 to make electric contact with the outer tube 340.

In operation of the detector 101, the body 220 additionally allows for the gas pressure within each holder to be greater or less than the pressure of gas at the probe tip 215. Gas will flow to or away from the probe accordingly. A gas is delivered to the body 220 from the gas supply 120 through the gas supply tube 125 and transfer tubes 420. A vacuum is created in the body 220 from the vacuum pump 130 through the vacuum tube 135 and transfer tubes 420. The gas or vacuum enters either the inner tube 320, insulator tube 330, or outer tube 340. The rubber gaskets 232 between each holder create a seal, and prevent gas from escaping between the holders. The gas or vacuum is then introduced into the inner tube 320, insulator tube 330, or outer tube 340 through one or more orifices 234 in each holder. The orifices 234 are approximately ⅛" in diameter or of a size to accommodate the required gas or vacuum. The gas is helium at 14 psi or any other inert gas at a pressure to meet the detectors needs. Alternatively, the gas supply 120 is a small (18 in³) cylinder of compressed helium such that a small, portable, battery-powered detection system is possible. Regulators in the gas supply tube 125 and vacuum tube 135 and the size of the orifices 234 (80 micron diameter hole in FIG. 8) are used to control the amount of gas flow. Gas flow rates and vacuums are adjusted for different detection target 110 environments.

Allowing multiple gas inputs/outputs enables the dilution of the gas in the detection target 110 entering the discharge area 630, creating a dilution-probe detection system. This is useful when sampling gases that cause the discharge to operate in an unstable manner. In this case, sampled gas is mixed with a stabilizing gas before entering the discharge region. The stabilizing gas may not need to be present in some situations, but in other operating environments, this may be the major constituent of the gas entering the discharge.

As an alternative, no gas or vacuum is needed, eliminating the need for gas supply 120, gas supply tube 125, vacuum pump 130, vacuum tube 135, or transfer tubes 420.

In operation of the detector 101, the probe 210 extends from the body 220 into the detection target 110. A gas is added around the fiber optic 310 if needed for protection from the detection target 110 atmosphere. A gas is also added around the fiber optic 310 if needed to achieve a stable discharge. A small amount of gas is also added inside the outer tube 340 as a purge to prevent condensation of contaminants in the outer tube 340. A vacuum is applied around the inner tube 320 and inside the insulator tube 330. The amount of vacuum being applied is regulated to cause an equal (or greater) quantity of gas to flow as is being supplied to the discharge area 630. The vacuum is required to maintain or lower the pressure in the discharge area 630 so the gas will enter the discharge area 630 from the detection target 110. Alternatively, no gas flow or vacuum is added to one or all tubes. In this case diffusion causes gas from the detection target 110 to enter the discharge area 630. Alternatively, a reduced amount or no vacuum is needed if the pressure in the detection target 110 is sufficient to supply gas to the discharge area 630 and then it will exit through one or more of the transfer tubes 420.

As an alternative, another tube is included surrounding the outer tube 340. Gas is applied to this additional tube to calibrate the detector. The calibration gas would enter the discharge area 630 due to a pressure differential established between various gases at orifices 234. When the calibration gas is not needed in this tube, it can be vented to allow gas to flow such that the detector can be used in a normal manner. The additional tube can also used to measure and monitor the pressure in the detection target 110 and discharge area 630.

An additional function of the inner tube 320, insulator tube 330, and outer tube 340 is to protect and support the fiber optic 310. Accordingly, sizes, thickness, and materials are adjusted to achieve this support.

The electrical potential applied between the inner tube 320 and outer tube 340 creates an electric discharge. The inner tube 320 and outer tube 340 serve as the electrodes and the insulator tube 330 insulates between them. The discharge point 610 or other structure in the inner tube 320 or outer tube 340 at the tip 215 creates a more stable discharge. The extension of the outer tube 340 past the fiber optic 310, inner tube 320, and insulator tube 330 provides protection to the fiber optic 310 from the discharge. The fiber optic 310 receives additional protection from the discharge by the extension of the inner tube 320 past the fiber optic 310. In this way, the discharge occurs in front of the fiber optic 310. If needed, additional protection is provided to the fiber optic 310 by applying an inert gas, as described above, to carry away particulates from the fiber optic, which reduce light transmission.

The light produced from the discharge area 630 enters the fiber optic 310. The light travels through the fiber optic 310 into the optical sensing device 140.

Figure 9:
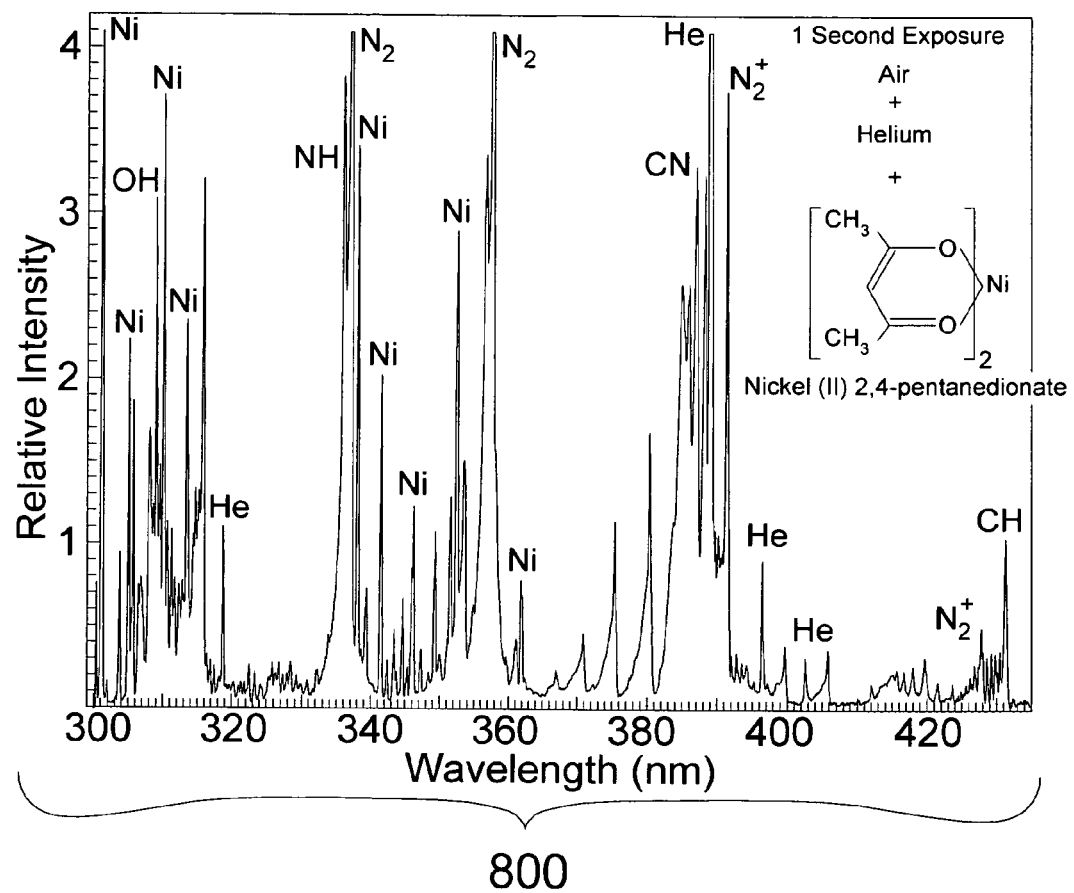
FIG. 9 illustrates an example of the data generated by optical sensing device according to an embodiment of the present invention.

FIG. 9 illustrates an example of the data generated by optical sensing device 140. The optical sensing device 140 provides sensing data 800 relating to the light intensity as a function of wavelength, also called a spectrum. The optical sensing device 140 is a spectrometer or other device capable of measuring the spectrum or the intensity of light produced in the discharge area 630. A small, battery-powered optical sensing device 140, operating at wavelengths somewhere between 200 nm to 1100 nm, provides adequate resolution for identification of many species in the discharge. However, when looking for the presence of a single chemical, a more compact and less-expensive optical sensing device 140 involves one or several spectral filters in combination with photodiodes to give intensity information at carefully chosen wavelengths corresponding to the emission of the desired chemical.

This sensing data 800 is used to identify types and concentrations of molecules in the discharge area 630. Each atom, or molecule, in the discharge area 630 will emit a unique spectral signature. This unique spectral signature is correlated to the type and concentrations of the molecules. Since the atmosphere in the discharge area 630 is that of the detection target 110 with only known additions of inert gasses, the molecular composition of the detection target 110 atmosphere is determined. The computer 155 is programmed to automatically identify molecules using the sensing data 800, and estimate the concentration based on tables generated by introducing known mixtures of molecules into the discharge area 630. As FIG. 9 shows, many atomic and diatomic spectral signatures indicate the presence of nickel (Ni), NH, nitrogen (impurity), CN, CH, and helium as the indicated molecule enters the discharge.

Light produced in the discharge area 630 also travels through the transparent insulator tube 330. This light is then visible through the view port 540 if the quartz insulator tube 330 is shaped appropriately. This light provides an additional means for monitoring and characterizing the properties of the discharge.

Theory of Operation

Described below is the theory of operation on which the detection system 100 is based. If this theory is shown not to accurately or completely describe the features of the invention that should in no way limit the invention described.

For this invention, molecular identification and quantification is based on emission spectroscopy. Emission spectroscopy typically entails creating an electric discharge in a gas under study and analyzing the gas based on the light emitted from the discharge. Just as neon signs give off a characteristic red-orange glow, indicating the presence of neon, every gas discharge gives different "colors" (visible and invisible) indicating the presence, concentration and pressure of the constituents. Most electrical gas discharges (neon signs, fluorescent lamps) operate at low pressure since stable macroscopic discharges are difficult to produce at pressures above several Torr (760 Torr is equivalent to one atmosphere pressure). Operating at sub-atmosphere pressures complicates emission measurements because reducing the gas pressure requires vacuum pumps and metering the gas flow such that the vacuum pump can maintain a low pressure in the discharge.

Described above is a novel technology for gas analysis at atmospheric pressure and higher. As the volume of the gas discharge region is reduced, the pressure can be increased to atmospheric pressure (and beyond) while still maintaining a stable discharge. This scaling law can be written as Pd=constant, where P is the gas pressure, and d a characteristic dimension in the discharge (tube diameter). If Pd is maintained at several Torr-Centimeters (typically 15 Torr cm), then the discharge is particularly stable and, at atmospheric pressure, has high energy density. The discharge is created at the end of a set of concentric tubes. Sufficient voltage is applied between the tubes to cause a visible glow of the gas, and the light is collected by a small fiber optic and delivered to a spectrometer and computer for analysis.

The spectrometer separates the light into different wavelengths (colors) and identifies the amount of light at each color. FIG. 9 demonstrates the power of emission spectroscopy using a microdischarge detector. This spectrum was taken to show that even organically bound metals could be detected. FIG. 8 illustrates the spectrum when Nickel 2,4 pentanedionate was placed in an oven and heated. When the compound was heated it vaporized, entering the discharge where many nickel atomic peaks were produced. Not only do specific peaks indicate the presence of nickel and helium (used as a dilution gas), but also the presence of CH, NH, nitrogen and water vapor (OH) as by-products of molecular breakdown. Every molecular and atomic species produces specific peaks, and the intensity of the peaks give the concentration under specific operating conditions.

The invention entails introducing gas in the detection target 110 (to be analyzed) into a high energy density gas discharge area 630 (plasma) where the gas molecules are broken down into atomic and diatomic constituents. These atomic and diatomic parts, in turn, emit light at specific wavelengths that can be used for their identification. The discharge is generated at the end of the tip 215, and light is collected from the discharge by the fiber optic 310 and delivered to the optical sensing device 140, and used for identifying unique properties of the gases entering the discharge. A key feature of the invention is the size, which allows the discharge to operate at atmospheric pressure in a stable manner. The small size also leads to a number of other desirable features such as supporting low (or no) gas flow (~0.1 SCCM), low power consumption (10 micro-watts to 1 watt), and low weight. In addition, power densities of over 100 kW/cc are achievable. This leads to increased performance by facilitating the breakdown of the sample gas and increased sensitivity by creating a significant amount of light for subsequent analysis. The materials of construction allow the discharge region to be operated in environments with temperatures in excess of 1100 degrees Celsius. This high-temperature operation opens up a number of uses previously impossible with other gas detection techniques.

The detector described here is capable of simultaneously detecting a multitude of different chemicals, including the detection of metals. These chemicals include NO, CO, CH, CN, CS, CCl, OH, SN, PH, PO, $N_2$, $C_2$, O, F, Cl, S, P, Ni, Al, Cu, Ag, Se, Cd, Hg, Pb, He, Ne, Ar, Kr, Xe, etc., and can identify whether compounds entering the discharge contain atoms such as S, P, F, H, Cl, As, Ni, Al, Ag, Au, Cu, Cr, Se, Cd, Hg, Pb, N, O, C, He, Ne, Ar, Kr, Xe, etc. An alternative sensing technique is to use electrical impedance measurements. Using electrical impedance measurements, no information is obtained about the make-up of the gas in the discharge, but relative changes can be noted as the gas composition changes in the detection target 110. This is useful for gas chromatography where it is important to monitor the changes in gas composition.

The system is economical, compact, and requires less supporting equipment than most detectors used in emissions monitoring.

Applications

The detector system 100 can be used in a wide variety of applications. Described below are three such alternative applications; stand-alone gas detector, trace impurity identification, and gas chromatography. Many more applications are possible.

Stand-Alone Gas Detection:

The detection system 100 is used to sense chemicals in the environment immediately surrounding the end of the tip 215. Since the probe 210 can be made relatively long (>1 meter) and can also withstand high temperatures, it can be placed in hostile environments (hot, high/low pressure, toxic, etc.) while the detector body 220, which contains rubber gaskets 232 remains in a relatively cool environment. With an appropriate filter covering the tip 215, the detector probe 210 could be placed into a detection target 110 such as a hot smokestack with toxic gas. The detector probe 210 passes through the wall of the stack to detect metals or other pollutants in the gas. Alternatively, the probe tip 215 is heated with an external heater (not shown) to temperatures in excess of 1000° C. to prevent soot and deposits from forming on the components of the tip 215 or probe 210. The probe 210 can be inserted into automotive or jet engine exhaust to look for concentrations of nitric oxide, oxygen, water vapor and other gases. The probe 210 can also be inserted in a detection target 110 with no moving gas, such as a closed cell. For instance, trace contaminants can be identified when they are within a pure noble gas, such as helium, neon, or argon; as they diffuse into the discharge area 630, they produce spectra identifying their presence and concentration.

Trace Impurity Identification:

The high-temperature operation can be used to identify impurities found in samples. Trace metal impurities have been identified in metal samples. In this application, the detector probe 210 is placed in an oven, along with the sample to be analyzed, in a background of inert gas (such as helium). The sample is then heated (to temperatures as high as 1100° C.), and as the vapor pressure of the impurities increase to give concentrations of approximately ten parts per billion (ppb) in the vapor phase around the detector, atomic emission is observed and used to identify the impurities contained in the sample. This technique has been used to identify the presence of impurities such as silver and copper in metal samples. As the temperature of the sample reached ~850° C., atomic emission was detected from silver atoms, and as the temperature climbed past 1000° C., atomic emission was detected from copper. Based on the vapor density of these compounds and oven size, a upper-bound could be placed on the quantity of the silver and copper impurities in the sample.

The detector can be placed in process gas streams to detect trace contaminants in an otherwise pure gas. This may be necessary in semiconductor processing gases where gas purity is of the utmost importance. Also, gas manufacturers can tell the quality and purity of gas being used to fill cylinders or tanks. One example is to detect trace contaminants in a pure helium gas stream. In this instance the detector could operate without the vacuum pump 130, gas supply 120, and gas supply tube 125 and vacuum tube 135 to create a simple gas detector without consumables.

Figure 10:
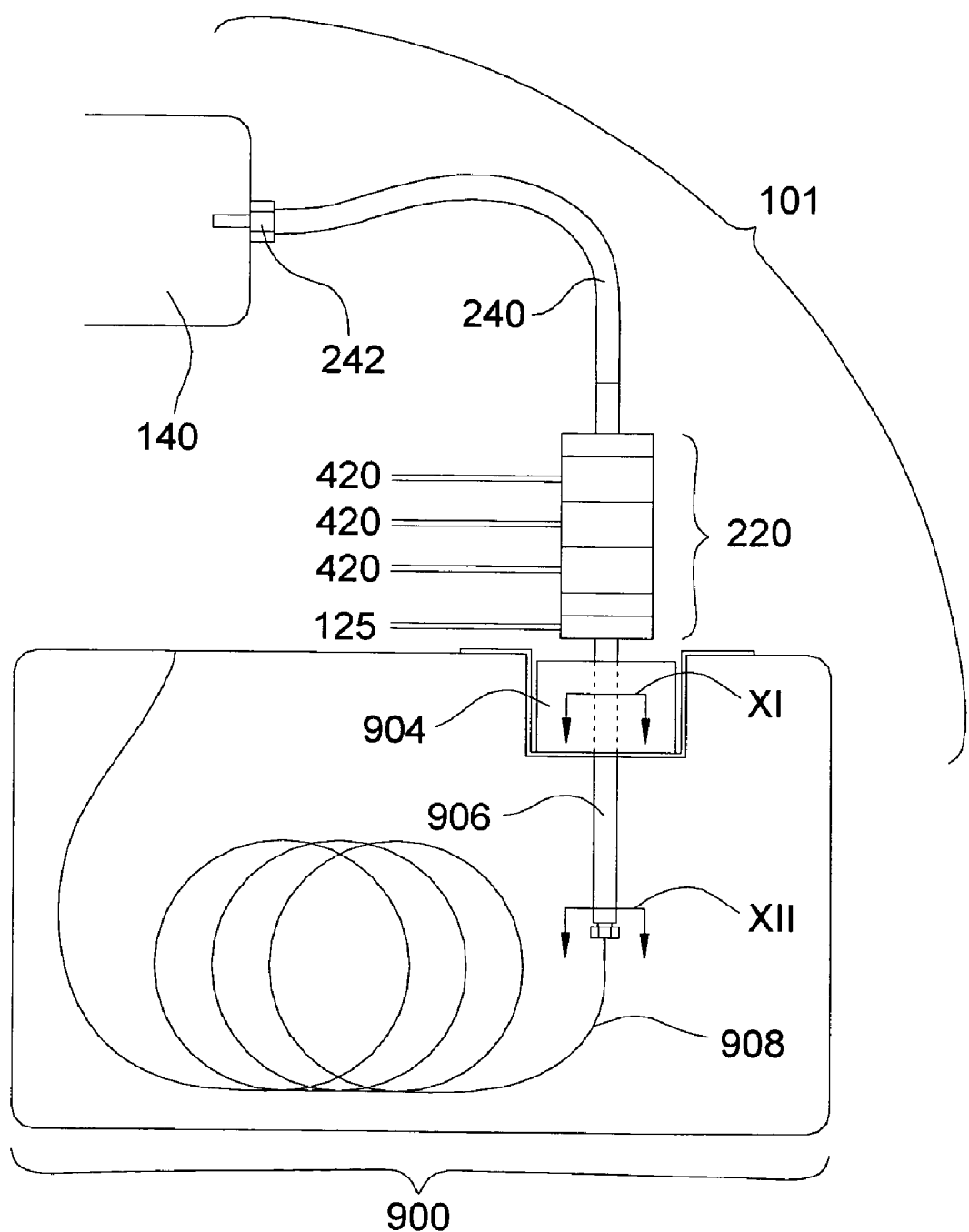
FIG. 10 illustrates the detector in an embodiment suitable for gas chromatography detection according to an embodiment of the present invention.

Gas Chromatography:

FIG. 10 illustrates the detector 101 in an embodiment suitable for gas chromatography detection, creating a gas chromatography detector 900. The gas chromatography detector 900 includes a detector 101, optical sensing device 140, additional gas supply tube 125, heater 904, support tube 906, and chromatograph column 908. The detector 101 is connected to the optical sensing device 140 and support tube 906. The support tube 906 is connected to the chromatograph column 908. The heater 904 surrounds a portion of the support tube 906. The detector body 220 has an additional gas supply tube 125.

Figure 11:
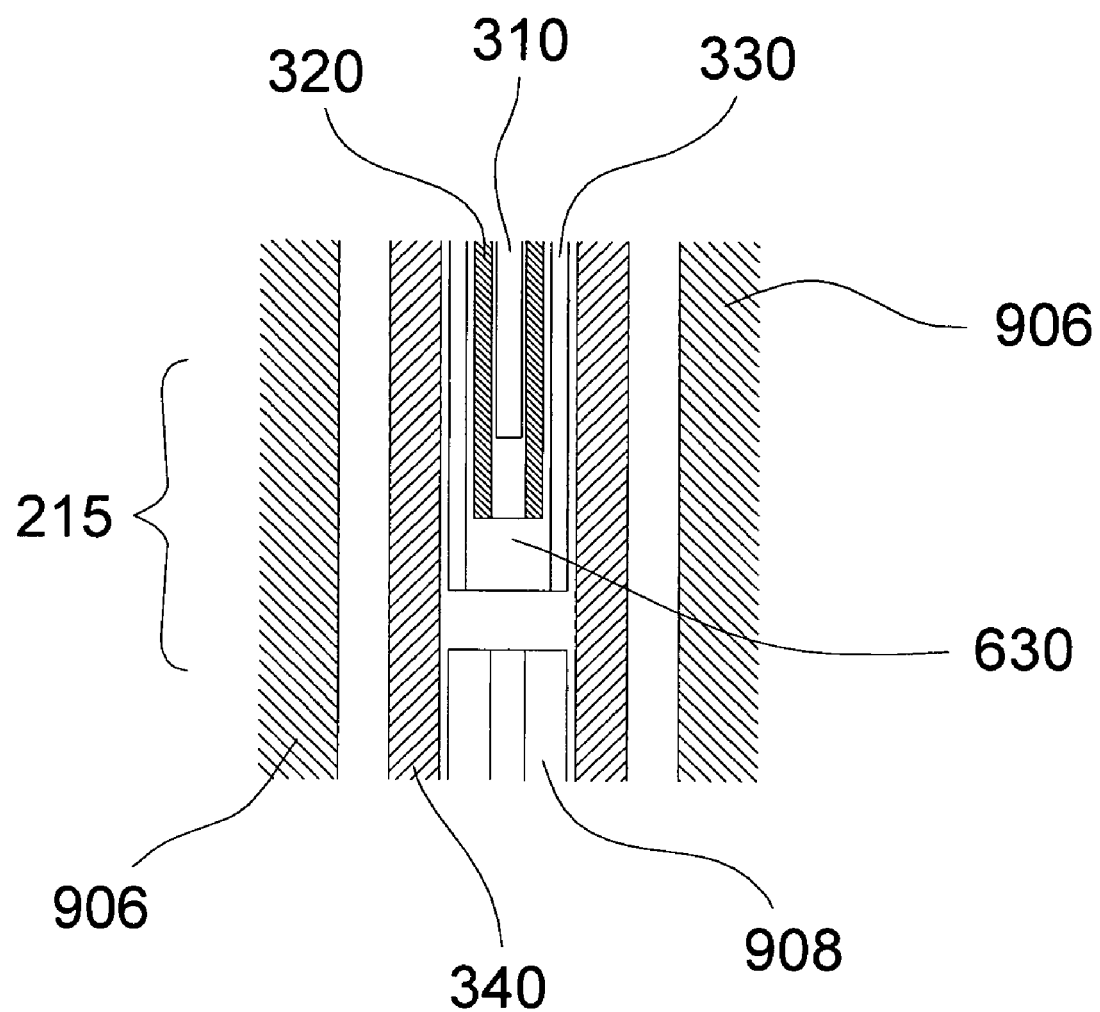
FIG. 11 illustrates a cross sectional view of a portion of the support tube inside the heater according to an embodiment of the present invention.

FIG. 11 is a cross section of a portion of the support tube 906 inside the heater 904. A portion of the chromatograph column 908 is inside the outer tube 340 and terminates. Beyond the termination of the chromatograph column 908 and inside the outer tube 340 is the detector tip 215.

Figure 12:
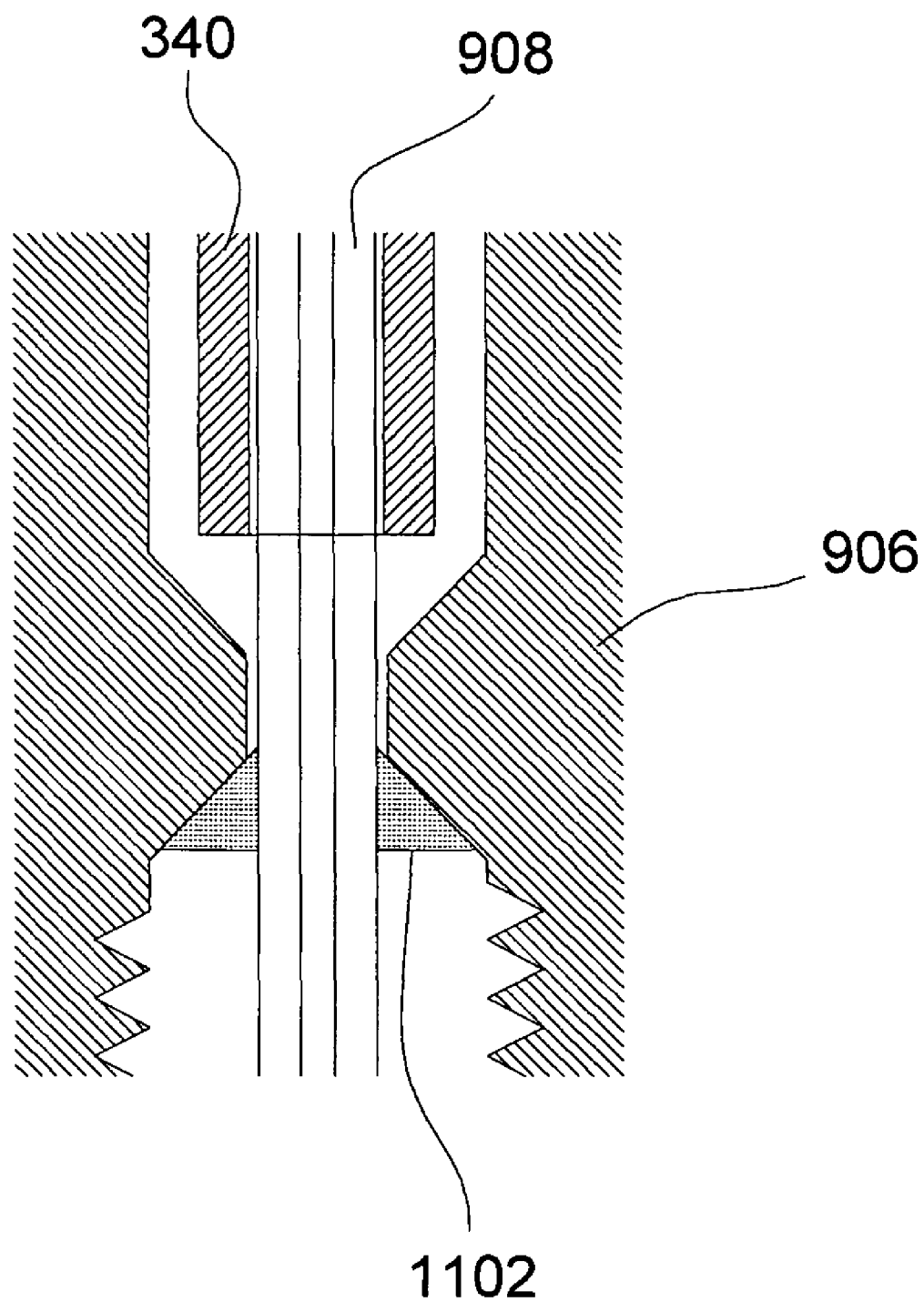
FIG. 12 illustrates a cross sectional view of a portion of the support tube.

FIG. 12 is a cross section of a portion of the support tube 906 above where the chromatograph column 908 extends past the support tube 906 and below where the chromatograph column 908 terminates inside the support tube 906. FIG. 12 shows that the gas chromatography detector 900 further includes a compression seal 1102. The outer tube 340 terminates in this portion of the support tube 906. The support tube 906 incorporates a compression seal around the chromatograph column 908 forming a gas-tight compression seal 1102.

In operation of the gas chromatography detector 900, gas is introduced through the additional gas supply tube 125 to increase the time response of the detector by flushing any "dead volume" in the detector tip 215. The gas entering the additional gas supply tube 125 travels between the outer tube 340 and support tube 906 to the compression seal 1102. At this point, the gas cannot flow between the chromatograph column 908 and support tube 906 because of the compression seal 1102, so the gas travels between outer tube 340 and chromatograph column 908. The compression seal 1102 is added to secure the chromatograph column 908 to the support tube 906 in a gas-tight manner. In the process of traveling, the gas has a chance to become pre-heated by the heater 904. The heater 904 keeps the discharge region hot to prevent condensation of the compounds eluding from the column (heater element and temperature sensor not shown). Once this gas reaches the end of the chromatograph column 908 near the discharge area 630, some of it exits through the detector 101 out the transfer tubes 420. A fiber purging gas is introduced through gas supply transfer tube 420, traveling between the fiber optic 310 and inner tube 320 to keep the fiber end clean. Gas flows can be relatively small, just enough to keep the fiber clean, and provide adequate time response in the detector.

This design makes the detector 101 easy to mate with existing gas chromatography equipment, particularly the Agilent 5890 and 6890 gas chromatographs. The support tube 906 provides a convenient means to fit the detector 101 to existing instruments. Fiber jacketing and terminator 242 are added to the optical output 240 to increase the ruggedness of the detector 101.

Figure 13:
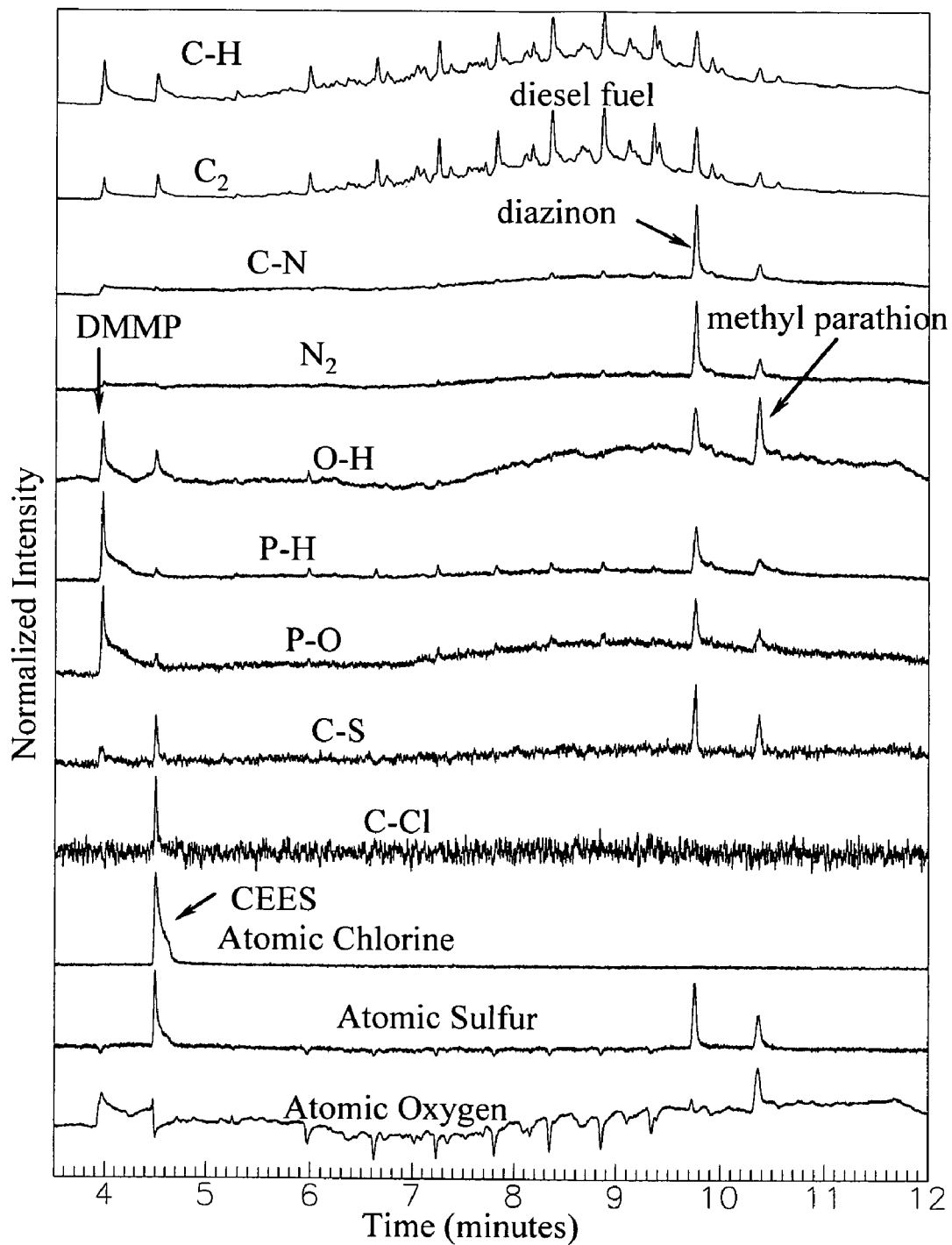
FIG. 13 illustrates twelve specific wavelength intensities from the spectrometer according to an embodiment of the present invention.

Gas chromatography is a particularly useful application of the detector system 100 technology. The power of this detection technique can be seen when looking at the spectra generated by the plasma as gases from a gas chromatograph separation column enter the discharge region. FIG. 13 illustrates twelve specific wavelength intensities, chromatographs, from the spectrometer over the course of 8½ minutes after a sample mixture of chemical agent simulants, with diesel fuel, were injected into the gas chromatograph injector chamber. The horizontal axis shows the time after injection, and the vertical axis shows the intensities of twelve different wavelengths, all acquired simultaneously by the detector system. Diesel fuel was added to the mixture to show the ability of this detector to selectively detect the chemical simulants when looking at specific wavelengths. Diesel fuel is a common interferrent for other detectors when looking for chemical warfare agents in practical situations, such as the battlefield. The injection was comprised of 100 nanograms (ng) of dimethyl methylphosphonate (DMMP), 100 ng of diazinon, 100 ng of methylparathion, 10 ng of 2-chloroethyl ethyl sulfide (CEES), 1 nanoliter (nL) of diesel fuel, and a balance of hexane solvent to make a 1 microliter (μL) injection. The horizontal axis is the time after the injection was made, and the vertical axis is the normalized intensity of twelve different wavelengths taken from the spectrometer on the microdischarge detector. All twelve chromatograms shown were taken at the same time, and each shows particular affinity to detect specific components eluding from the column. The first chemical to elude from the column is DMMP at about four minutes. Next, CEES enters the discharge detector at approximately 4.5 minutes. Between five and eleven minutes the different chemicals comprising diesel fuel elude from the column. Diazinon and methyl parathion exit the column at approximately 9.75 and 10.4 minutes respectively.

The top two chromatograms show light intensity from emission from the molecules CH and $C_2$. Since all molecules in the injected mixture contain multiple carbon and hydrogen atoms, peaks are present in these chromatograms for every compound exiting the column. However, the remaining ten chromatograms have particular strengths for picking out the four chemical agent simulants over the diesel fuel. For instance, CEES is the only chemical that contains chlorine, and thus, the chromatograms taken from line intensities associated with the chlorine atom (CCl and atomic chlorine) only show a peak as CEES enters the discharge. DMMP contains no sulfur, nor does diesel fuel, and when looking at line intensities associated with sulfur (CS, and atomic sulfur) only the chemicals with sulfur appear (CEES, diazinon, and methyl parathion). Conversely, CEES contains no phosphorous, but DMMP, diazinon and methyl parathion do contain phosphorus, thus they appear when looking at wavelengths associated with phosphorous. The only molecules that contain nitrogen are diazinon and methyl parathion, and they produce the predominant peaks when looking at line intensities for CN and $N_2$. Finally, both DMMP and methyl parathion have a doubly-bonded oxygen and increase the atomic oxygen concentration when entering the discharge, while all the other compounds tend to reduce the available atomic oxygen or produce little change.

The composition information given with this detector combined with the column retention time give more data than is capable with most detection techniques. This allows for unique chemical identification in most cases, with low false positives.

Thus the reader will see that this invention provides a detector that is preferable over other, previously known, detectors. While the above description contains many specificities, these should not be construed as limitations on the scope of the invention but rather as an explanation of one preferred embodiment thereof. Many other variations are possible. Accordingly the scope of the invention should be determined not by the embodiment illustrated but by the appended claims and their legal equivalents.

What is claimed is:

1. A device for detection of atomic and molecular compositions comprising:

a) a first electrode tubular in shape;

b) a second electrode tubular in shape wherein the second electrode extends past the first electrode, the first electrode is positioned inside the second electrode;

c) an insulation layer between the first electrode and the second electrode;

d) a means for applying an electrical voltage between the first electrode and second electrode in order to generate an electrical current between the electrodes; and e) a means for measuring the electrical and/or optical properties of a discharge generated as the result of the electrical current between the first electrode and second electrode.

2. The device of claim 1, wherein the measured property is impedance.

3. The device of claim 1, further comprising a fiber optic positioned to transmit light from the discharge generated as the result of the electrical current between the first electrode and the second electrode.

4. The device of claim 3, wherein the fiber optic is disposed inside the first electrode.

5. The device of claim 4, wherein the first electrode extends past the fiber optic.

6. The device of claim 3, wherein the means for measuring the optical properties is a spectrometer.

7. The device of claim 1, wherein the insulation layer comprises an insulating coating on an outer surface of the first electrode.

8. The device of claim 1, wherein said insulation layer comprises a dielectric tube between the second electrode and first electrode.

9. The device of claim 8, further comprising a means for supplying a gas flow.

10. The device of claim 9, wherein the gas flow travels between the first electrode and the insulation layer.

11. The device of claim 9, wherein the gas flow travels between the second electrode and the insulation layer.

12. The device of claim 8, further comprising a means for supplying a vacuum.

13. The device of claim 12, wherein the vacuum is applied between the first electrode and the insulation layer.

14. The device of claim 12, wherein the vacuum is applied between the second electrode and the insulation layer.

15. The device of claim 1, wherein the end of the first electrode is sharpened to a point.

16. The device of claim 1, wherein the first electrode further comprises a hole in the vicinity of a discharge.

17. The device of claim 1, further comprising a means for supplying a gas flow.

18. The device of claim 1, further comprising a means for supplying an inert gas flow.

19. The device of claim 1, further comprising a means for supplying a vacuum.

20. The device of claim 1, further comprising a data analysis component.

21. The device of claim 1, further comprising a gas chromatograph.

22. The device of claim 1, wherein the electrical voltage is applied continuously.

23. The device of claim 1, wherein the electrical voltage is applied cyclically.

24. The device of claim 1, wherein the device can be used under severe conditions for gas composition analysis, including temperatures in excess of 1100° C., toxic or corrosive environments, and pressures from one to two thousand Torr.

25. A gas chromatograph comprising:

i. a column comprising an inner tube, an outer tube, and a seal terminating the outer tube;

ii. a device for the detection of molecular compositions positioned at the end of the column comprising:

i) a first electrode tubular in shape;

ii) a second electrode tubular in shape wherein the second electrode extends past the first electrode, the first electrode is positioned inside the second electrode;

iii) an insulation layer between the first electrode and the second electrode;

iv) a means for applying an electrical voltage between the first electrode and second electrode; and v) a means for measuring the optical properties of a discharge generated as the result of the electrical voltage between the first electrode and second electrode; and iii. a support for holding the column and device for the detection of molecular compositions in relative position to each other.

26. The device of claim 25, further comprising a fiber optic positioned to transmit light from the discharge generated as the result of the electrical voltage between the first electrode and the second electrode.

27. The device of claim 26, wherein the fiber optic is disposed inside the first electrode.

28. The device of claim 27, wherein the first electrode extends past the fiber optic.

29. The device of claim 25, wherein the means for measuring the optical properties is a spectrometer.

30. The device of claim 25, wherein the insulation layer comprises an insulating coating on an outer surface of the first electrode.

31. The device of claim 25, wherein said insulation layer comprises a dielectric tube between the second electrode and first electrode.

32. The device of claim 31, further comprising a means for supplying a gas flow.

33. The device of claim 32, wherein the gas flow travels between the first electrode and the insulation layer.

34. The device of claim 32, wherein the gas flow travels between the second electrode and the insulation layer.

35. The device of claim 31, further comprising a means for supplying a vacuum.

36. The device of claim 35, wherein the vacuum is applied between the first electrode and the insulation layer.

37. The device of claim 35, wherein the vacuum is applied between the second electrode and the insulation layer.

38. The device of claim 25, wherein the end of the first electrode is sharpened to a point.

39. The device of claim 25, wherein the first electrode further comprises a hole in the vicinity of a discharge.

40. The device of claim 25, further comprising a means for supplying a gas flow.

41. The device of claim 25, further comprising a means for supplying an inert gas flow.

42. The device of claim 25, further comprising a means for supplying a vacuum.

43. The device of claim 25, further comprising a data analysis component.

* * * * *